US011857658B2

(12) United States Patent
Hwang et al.

(10) Patent No.: US 11,857,658 B2
(45) Date of Patent: Jan. 2, 2024

(54) COSMETIC COMPOSITIONS WITH ENHANCED COLOR RETENTION FOR IMPROVED SKIN APPEARANCE

(71) Applicant: Edgewell Personal Care Brands, LLC, Chesterfield, MO (US)

(72) Inventors: Hiu-Ing Donna Hwang, Leonia, NJ (US); Grace Riccardi, Jersey City, NJ (US)

(73) Assignee: Edgewell Personal Care Brands, LLC, Chesterfield, MO (US)

(*) Notice: Subject to any disclaimer, the term of this patent is extended or adjusted under 35 U.S.C. 154(b) by 0 days.

(21) Appl. No.: 14/723,650

(22) Filed: May 28, 2015

(65) Prior Publication Data
US 2015/0342845 A1 Dec. 3, 2015

Related U.S. Application Data

(60) Provisional application No. 62/004,546, filed on May 29, 2014.

(51) Int. Cl.
| | |
|---|---|
| *A61K 8/35* | (2006.01) |
| *A61K 8/87* | (2006.01) |
| *A61K 8/92* | (2006.01) |
| *A61K 8/25* | (2006.01) |
| *A61K 8/81* | (2006.01) |
| *A61K 8/31* | (2006.01) |
| *A61K 8/37* | (2006.01) |
| *A61K 8/60* | (2006.01) |
| *A61K 8/96* | (2006.01) |
| *A61Q 1/02* | (2006.01) |
| *A61Q 17/04* | (2006.01) |

(52) U.S. Cl.
CPC ........... *A61K 8/35* (2013.01); *A61K 8/25* (2013.01); *A61K 8/31* (2013.01); *A61K 8/37* (2013.01); *A61K 8/375* (2013.01); *A61K 8/602* (2013.01); *A61K 8/8152* (2013.01); *A61K 8/8182* (2013.01); *A61K 8/87* (2013.01); *A61K 8/922* (2013.01); *A61K 8/96* (2013.01); *A61Q 1/02* (2013.01); *A61Q 17/04* (2013.01); *A61K 2800/43* (2013.01); *A61K 2800/594* (2013.01)

(58) Field of Classification Search
CPC ... A61K 8/35; A61K 8/25; A61K 8/31; A61K 8/37; A61K 8/375; A61K 8/602; A61K 8/8152; A61K 8/8182; A61K 8/87; A61K 8/922; A61K 8/96; A61Q 1/02; A61Q 17/04
See application file for complete search history.

(56) References Cited

U.S. PATENT DOCUMENTS

| | | | |
|---|---|---|---|
| 5,087,445 A * | 2/1992 | Haffey | A61K 8/445 |
| | | | 424/59 |
| 6,313,181 B1 | 11/2001 | Cohen et al. | |
| 6,517,823 B1 * | 2/2003 | Norman | A61K 8/39 |
| | | | 424/400 |
| 6,576,702 B2 * | 6/2003 | Anderle | A61K 8/87 |
| | | | 524/591 |
| 6,780,402 B1 | 8/2004 | Agostini | |
| 7,022,316 B2 | 4/2006 | Galdi et al. | |
| 7,108,860 B2 | 9/2006 | Dueva et al. | |
| 7,820,150 B2 * | 10/2010 | Kohlhase | A61K 8/0212 |
| | | | 424/401 |
| 8,124,060 B2 * | 2/2012 | Feng | A61K 8/81 |
| | | | 424/69 |
| 8,128,919 B2 | 3/2012 | Fleissman | |
| 8,691,192 B1 | 4/2014 | Halpern et al. | |
| 2003/0044364 A1 * | 3/2003 | Meyer | A61K 8/27 |
| | | | 424/59 |
| 2007/0207222 A1 | 9/2007 | Yu et al. | |
| 2007/0269389 A1 * | 11/2007 | Fuscelli Pytel | A61K 8/0229 |
| | | | 424/59 |
| 2008/0025922 A1 | 1/2008 | Marrs | |
| 2009/0221978 A1 * | 9/2009 | Gatto | A61L 15/34 |
| | | | 604/367 |
| 2009/0264587 A1 * | 10/2009 | Blum | C08G 18/0823 |
| | | | 524/591 |
| 2012/0171266 A1 * | 7/2012 | Cantwell | A61K 8/8152 |
| | | | 424/401 |
| 2012/0195839 A1 * | 8/2012 | He | A61K 8/046 |
| | | | 424/59 |
| 2013/0028851 A1 * | 1/2013 | Fontaine | A61K 8/27 |
| | | | 424/59 |

(Continued)

FOREIGN PATENT DOCUMENTS

| | | |
|---|---|---|
| CN | 1444471 A | 9/2003 |
| CN | 101505718 A | 8/2009 |

(Continued)

OTHER PUBLICATIONS

International Cosmetic Ingredient Dictionary and Handbook. 6th edition, 2016. 61 pages.*
Safety Assessment of Polyurethanes as Used in Cosmetics. The 2017 Cosmetic Ingredient Review Expert Panel. 1-40p. (Year: 2017).*
International Preliminary Report on Patentability issued from corresponding application PCT/US2015/032842 dated Nov. 29, 2016.
Australian Examination Report No. 1 issued from corresponding application AU2015266930 dated Aug. 14, 2019.
Unofficial translation of Japanese Notice of Allowance issued in connection with corresponding Japanese Patent Application No. 2017-515010 dated Jan. 2, 2020.

(Continued)

*Primary Examiner* — Robert A Wax
*Assistant Examiner* — Olga V. Tcherkasskaya

(57) ABSTRACT

A cosmetic composition with enhanced water resistance, color intensity and color retention after exposure to water is disclosed herein. The composition comprises a water dispersible film former component, a skin adhesion promoter component, a color enhancer component, and one or more colorants. The synergy of the components contributes to the improved attributes of the composition.

39 Claims, No Drawings

(56) References Cited

U.S. PATENT DOCUMENTS

| | | | | |
|---|---|---|---|---|
| 2013/0028853 A1* | 1/2013 | Nurse | ........................ | A61K 8/35 424/60 |
| 2013/0189204 A1* | 7/2013 | Duggal | ..................... | A61K 8/35 424/59 |
| 2013/0243834 A1* | 9/2013 | Tanner | ...................... | A61K 8/26 424/401 |
| 2013/0280189 A1* | 10/2013 | Thomas | ................. | A61K 8/895 424/59 |

FOREIGN PATENT DOCUMENTS

| | | | |
|---|---|---|---|
| CN | 102333518 | A | 1/2012 |
| CN | 102596153 | A | 7/2012 |
| JP | 2009084188 | A | 4/2009 |
| JP | 2010-501515 | A | 1/2010 |
| JP | 2010202527 | A | 9/2010 |
| JP | 2010248102 | A | 11/2010 |
| JP | 2013-506629 | A | 2/2013 |
| JP | 2013510153 | A | 3/2013 |
| JP | 2013-534218 | A | 9/2013 |
| JP | 2013253046 | A | 12/2013 |
| WO | 9621422 | A1 | 7/1996 |
| WO | 9701321 | A1 | 1/1997 |
| WO | 03103615 | A1 | 12/2003 |
| WO | 2006113882 | A1 | 10/2006 |

OTHER PUBLICATIONS

EP Search Report and Opinion issued in connection with corresponding EP Application No. 15800190.9 dated Apr. 7, 2017.
Unofficial translation of Chinese Office Action and Search Report issued in connection with corresponding CN Application No. 201580040592.2 dated Jul. 22, 2019.
Unofficial translation of Japanese Office Action issued in connection with corresponding JP Application No. 2017-515010 dated May 24, 2019.
International Search Report and Written Opinion issued in connection with corresponding PCT Application No. PCT/US2015/032842 dated Aug. 28, 2015.

* cited by examiner

COSMETIC COMPOSITIONS WITH ENHANCED COLOR RETENTION FOR IMPROVED SKIN APPEARANCE

CROSS REFERENCE TO RELATED APPLICATIONS

This application claims the benefit of U.S. Provisional Patent Application Ser. No. 62/004,546, filed on May 29, 2014, the content of which is incorporated herein for reference in its entirety.

BACKGROUND OF THE INVENTION

A. Field of Endeavor

The present invention relates to cosmetic compositions that enhance skin appearance with improved water resistance, color intensity, color retention, and skin feel.

B. Background Information

The busy consumer prefers multi-functional cosmetic compositions that can provide sun protection, good color intensity, good color retention, water and/or sweat resistance, all while demanding a product that feels good on the skin. Traditional color cosmetic compositions provide many of these enhanced qualities, but there can be drawbacks in composition feel that reduce the consumer's consistent use of these products. For example, while a composition may have excellent color intensity and color retention on the skin, there is insufficient water resistance. Or the composition may have excellent water resistance and sun protection, but the skin feel is poor leading to low consumer compliance in using the product in a manner to sufficiently provide maximum sun protection.

Emulsifiers are often used to provide that good skin feel with cosmetic compositions. Emulsifiers stabilize the emulsion for either water in oil (w/o) or oil in water (o/w) cosmetic compositions. However, when the user engages in water sports or activities the emulsifiers easily re-emulsify with moisture thereby diminishing the water resistance of the compositions. Furthermore, any colorants are also easily transferred onto clothing or towels. As a result, any actives or colorants are washed off by the water and the products fail to provide the specified functionality. Adding a film former can be a solution for this problem. However, the required concentration of the film former for both actives and colorants is very high due to the difficulty in formulating water-insoluble components. The high level of film formers results in a product that is tacky and difficult to spread during application compromising the good skin feel. However, the level of film former to achieve good skin feel cannot successfully retain actives or color on the skin after contact with water.

Furthermore, when consumers use cosmetic compositions with a colorant, they expect the composition to provide both good color intensity and good color retention, even after water exposure.

SUMMARY

The present invention is directed, in a first aspect, to a cosmetic composition comprising a water dispersible film former component; a skin adhesion promoter component; a color enhancer component; and one or more colorants.

The water dispersible film former may preferably be selected from the group consisting of acrylate/$C_{12-22}$ methacrylate copolymer; polypropylene glycol ("PPG")-17/isophorone diisocyanate ("IPDI")/dimethylol propionic acid copolymer; Polyurethane-32; Polyurethane-34; Polyurethane-35; Polyurethane-48; hydrolyzed wheat protein/polyvinyl pyrrolidone ("PVP") crosspolymers; maltodextrin/vinyl pyrolidone ("VP") copolymer; butylated PVP copolymer; VP/polycarbamylpolyglycol ester; VP/dimethylaminoethylmethacrylate/polycarbamyl polyglycol ester; VP/Dimethiconyl-acrylate/polycarbamyl polyglycol ester; and combinations thereof. More preferably, the water dispersible film former is acrylate/$C_{12-22}$ methacrylate copolymer; PPG-17/IPDI/dimethylol propionic acid ("DMPA") copolymer; Polyurethane-34; VP/polycarbamyl polyglycol ester; or combinations thereof. Most preferably, the water dispersible film former is acrylate/$C_{12-22}$ methacrylate copolymer. The water dispersible film former may be present in an amount of about 0.01 to about 30.0 wt. % based on a total weight of the composition.

The skin adhesion promoters can be hydrophobic, hydrophilic, or a combination thereof. When the skin adhesion promoter is hydrophobic, it may be selected from the group consisting of polydiethylene glycol adipate/IPDI copolymer; hydrogenated castor Oil/IPDI copolymer; polyglyceryl-2 diisostearate/IPDI copolymer; glyceryl diricinoleate/IPDI copolymer; propylene glycol diricinoleate/IPDI copolymer; dimethiconol/IPDI copolymer (and) cyclomethicone; bis-PPG-15 dimethicone/IPDI copolymer; PPG-12/SMDI copolymer; adipic acid/diglycol crosspolymer; trimethylpentanediol/adipic acid/glycerin crosspolymer; Polyester-10 (and) propylene glycol dibenzoate; Polyester-7 (and) neopentylglycol polyester; VP/hexadecene copolymer, VP/eicosene copolymer, tricontanyl PVP; acrylic acid/isobornylmethacrylate/isobutylmethacrylate copolymer/isododecane in isododecane; behenyl methacrylate/t-butyl methacrylate copolymer in isododecane; hydrogenated polyisobutene; hydrogenated polycyclopentadiene; petrolatum (and) ethylene/propylene/styrene copolymer, butylene/ethylene/styrene copolymer; and combinations thereof.

When the skin adhesion promoter is hydrophilic, it may be selected from the group consisting of polyethylene glycol ("PEG")-40 hydrogenated castor oil/IPDI copolymer; PEG-200 hydrogenated castor oil/IPDI copolymer; glycereth-7/hydroxystearate/IPDI copolymer; bis-PPG-15 dimethicone/IPDI copolymer; Polyurethane-18; and combinations thereof.

Preferably, the skin adhesion promoter comprises polydiethyleneglycol adipate/isophorone diisocyanate copolymer; Polyester-7 (and) neopentylglycol polyester; VP/eicosene copolymer; hydrogenated polyisobutene (and) butylene/ethylene/styrene copolymer (and) ethylene/propylene/styrene copolymer; bis-PPG-15 dimethicone/IPDI copolymer; Polyurethane-18; or combinations thereof. The skin adhesion promoter is preferably present in an amount of about 0.05 wt. % to about 15.0 wt. % based on a total weight of the composition.

The color enhancer of the composition comprises a silicon material. Preferably, the silicon material is selected from the group consisting of silicone resins, silicone cross-polymers, silicone copolymers, silicone elastomers, silicone resin elastomer gels, silica, fumed silica, amorphous silica, silica dimethyl silylates, hydrophobic modified silica, hydrated silica, silicates, and combinations thereof. The silicone resin may preferably comprise trimethylsiloxysilicate/polypropylsilsesquioxane silicone resin; polymethylsilsesquioxane; polyphenylsilsesquioxane; $C_{30-45}$ alkyl dimethylsilyl polypropylsilsesquioxane; dimethicone (and) polysilicone-11 crosspolymer; dimethicone (and) cetearyl dimethicone crosspolymer; dimethicone (and) dimethicone crosspolymer; stearoxymethicone/dimethicone copolymer; dimethicone (and) vinyldimethyl/trimethylsiloxysilicate/dimethicone crosspolymer; or combinations thereof. The color enhancer may also comprise silica selected from the group consisting of hydrated silica, fumed silica, pyrogenic silica, hydrophobic modified silica; or combinations thereof. Preferably, the weight ratio of the color enhancer to the one or more colorants is about 1:50 to about 1:0.05.

The one or more colorants of the present invention may comprise hennas, caramels, malva extracts, hibiscus extracts, tyrosines, green teas, glyceraldehydes, ginsengs, erythruloses, iron oxides, annattos, ultramarine pigments, beta-carotenes, carmines, chrome oxides, titanium oxide, zinc oxide, bismuth compounds, Food, Drug, and Cosmetic Grade ("FD&C") water-soluble dyes, copper powders, guanines, walnut extracts, iron oxides, micas, and combinations thereof. Preferably, the one or more colorant comprises hennas, caramels, micas, pearl pigments, pearlescent pigments, and combinations thereof.

Preferably, the cosmetic composition of the present invention further includes one or more photoactives. The one or more photoactives ma be selected from the group consisting of p-aminobenzoic acid and derivatives thereof; butyl methoxydibenzoylmethane; benzophenones; hydroxy-substituted benzophenones; methoxy-substituted benzophenones; benzophonone-1; benzophenone-2; benzophenone-3; benzophenone-4; benzophenone-6; benzophenone-8; benzophenone-12; methoxycinnamate; ethyl dihydroxypropyl-p-aminobenzoate; glyceryl-p-aminobenzoate; homosalate; methyl anthranilate; octocrylene; octyl dimethyl-p-aminobenzoate; octyl methoxycinnamate; octyl salicylate; 2 phenylbenzimidazole-5-sulphonic acid; triethanolamine salicylate; 3-(4-methylbenzylidene)-camphor; red petrolatum, 3-(4-methylbenzyldine)boran-2-one(methylbenzindinecamphor); benzotriazole; salicylates; phenylbenzimidazole-5-sulfonic acid; methylene bis-benzotriazolyl tetramethylbutyl phenol; avobenzone; 4-isopropyldibenzoylmethane; butyl-methoxydibenzoylmethane; octocrylene; octisalate; oxybenzone; bis-ethylhexyloxyphenol methoxy triazine; 4-isopropyl-dibenzoylmethane; metal oxides; zinc oxide; octyltriethoxy silanol; titanium dioxide; alumina; triethoxy silane; and combinations thereof.

In another aspect, the present invention is directed to a sunscreen composition comprising one or more photoactives; a water dispersible film former comprising an acrylate/$C_{12-22}$ alkylmethacrylate copolymer, PPG-17/IPDI/DMPA copolymer, Polyurethane-34, VP/polycarbamyl polyglycol ester, or combinations thereof; a skin adhesion promoter comprising polydiethyleneglycol adipate/isophorone diisocyanate copolymer, Polyester-7 (and) neopentylglycol polyester, VP/eicosene copolymer, hydrogenated polyisobutene (and) butylene/ethylene/styrene copolymer (and) ethylene/propylene/styrene copolymer, bis-PPG-15 dimethicone/IPDI copolymer, Polyurethane-18, or combinations thereof; a color enhancer comprising silicone resins, silicone crosspolymers, silicone copolymers, silicone elastomers, silicone resin elastomer gels, silica, fumed silica, amorphous silica, silica dimethyl silylates, hydrophobic modified silica, hydrated silica, silicates, or combinations thereof; and one or more colorants.

Preferably, the one or more photoactives is selected from the group consisting of homosalate; octisalate; octocrylene; avobenzone; oxybenzone; bis-ethylhexyloxyphenol methoxyphenyl triazine; octyltriethoxy silanol; triethoxysilane; titanium dioxide; zinc oxide; alumina; and combinations thereof. Most preferably, the one or more photoactives comprises homosalate, octisalate, homosalate, octocrylene, avobenzone, or combinations thereof. The one or more photoactives are present in an amount of about 0.1 wt. % to about 40.0 wt. % based on a total weight of the composition.

Preferably, the water dispersible film former is present in an amount of about 0.01 wt. % to about 30.0 wt. % based on a total weight of the composition. More preferably, the water dispersible film former is present in an amount of about 0.1 wt. % to about 10.0 wt. % based on a total weight of the composition. Most preferably, the water dispersible film former is present in an amount of about 0.5 wt. % to about 3.0 wt. % based on a total weight of the composition.

Preferably, the skin adhesion promoter is present in a weight ratio of about 1:150 to about 1:0.1 to the photoactives of the sunscreen composition. More preferably, the skin adhesion promoter is present in a weight ratio of about 1:80 to about 1:1 to the photoactives of the sunscreen composition.

Preferably, the color enhancer is present in a weight ratio of about 1:50 to about 1:0.05 to the colorants. More preferably, the color enhancer is present in a weight ratio of about 1:10 to about 1:0.1 to the colorants. Most preferably, the color enhancer is present in a weight ratio of about 1:4 to about 1:0.4 to the colorants.

Preferably, the one or more colorants comprise hennas, caramels, malva extracts, hibiscus extracts, tyrosines, green teas, glyceraldehydes, ginsengs, erythruloses, ferric compounds (including iron oxide), annattos, ultramarine pigments, beta-carotenes, carmines, chrome oxides, titanium oxide, zinc oxide, bismuth compounds, FD&C water-soluble dyes, copper powders, guanines, walnut extracts, iron oxides, micas, or combinations thereof. More preferably, the one or more colorants comprise hennas, caramels, micas, pearl pigments, pearlescent pigments or combinations thereof. The one or more colorants are present in an amount of about 0.01 wt. % to about 20.0 wt. % based on a total weight of the composition. More preferably, the one or more colorants are present in an amount of about 0.05 wt. % to about 10.0 wt. % based on a total weight of the composition. Most preferably, the one or more colorants are present in an amount of about 0.05 wt. % to about 2.5 wt. % based on a total weight of the composition.

In yet another embodiment, the present invention is directed to a sunscreen composition comprising one or more photoactives in an amount sufficient to provide an Sun Protection Factor ("SPF") of 4 to 30; a water dispersible film former comprising an acrylate/$C_{12-22}$ alkylmethacrylate copolymer, PPG-17/IPDI/DMPA copolymer, Polyurethane-34, VP/polycarbamyl polyglycol ester, or combinations thereof; a skin adhesion promoter comprising polydiethyleneglycol adipate/isophorone diisocyanate copolymer, Polyester-7 (and) neopentylglycol polyester, VP/eicosene copolymer, hydrogenated polyisobutene (and) butylene/ethylene/styrene copolymer (and) ethylene/propylene/styrene copolymer, bis-PPG-15 dimethicone/IPDI copolymer, Polyurethane-18, or combinations thereof; a color enhancer comprising silicone resins, silicone cross-polymers, silicone copolymers, silicone elastomers, silicone resin elastomer gels, silica, fumed silica, amorphous silica, silica dimethyl silylates, hydrophobic modified silica, hydrated silica, silicates, or combinations thereof; and one or more colorants.

Preferably, the water dispersible film former is present in an amount of about 0.5 wt. % to about 3.0 wt. % based on a total weight of the composition; the skin adhesion promoter is present in an amount of about 0.1 wt. % to about 3.0 wt. % based on a total weight of the composition; the color enhancer is present in an amount of about 0.2 wt. % to about 2.5 wt. % based on a total weight of the composition.

This embodiment may further include one or more additives selected from the group consisting of cosmetically acceptable carriers, oils, sterols, amino acids, moisturizers, powders, colorants, pH adjusters, perfumes, essential oils, cosmetic active ingredients, vitamins, essential fatty adds, sphingolipids, self-tanners, excipients, fillers, emulsifying agents, antioxidants, surfactants, chelating agents, gelling agents, thickeners, emollients, humectants, moisturizers, minerals, viscosity modifiers, rheology modifiers, keratolytics, retinoids, hormonal compounds, alpha-hydroxy acids, alpha-keto acids, anti-mycobacterial agents, anti-fungal agents, anti-microbials, anti-virals, analgesics, anti-allergenic agents, antihistamines, anti-inflammatory agents, anti-irritants, anti-neoplastics, immune system boosting agents, immune system suppressing agents, anti-acne agents, anesthetics, antiseptics, insect repellents, skin cooling compounds, skin protectants, skin penetration enhancers, exfoliants, lubricants, fragrances, colorants, staining agents, depigmenting agents, hypopigmenting agents, preservatives, stabilizers, pharmaceutical agents, photostabilizing agents, and spherical powders.

Preferably, the sunscreen composition has an SPF of 4 and the one or more photoactive comprise octisalate, octocrylene and avobenzone is present in an amount of about 2.0 wt. %. Preferably, the sunscreen composition has an SPF of 8 and the one or more photoactive comprise octisalate, octocrylene and avobenzone is present in an amount of about 5.0 wt. %. Preferably, the sunscreen composition has an SPF of 15 and the one or more photoactive comprise octisalate, octocrylene and avobenzone is present in an amount of about 8.0 wt. %. Preferably, the sunscreen composition has an SPF of 30 and the one or more photoactive comprise homosalate, octisalate, octocrylene and avobenzone is present in an amount of about 13.0 wt, %.

In yet another embodiment, the present invention is directed to a sunscreen composition consisting essentially one or more photoactives in an amount sufficient to provide an SPF of 4 to 30; a water dispersible film former comprising an acrylate/$C_{12-22}$ alkylmethacrylate copolymer, PPG-17/IPDI/DMPA copolymer, Polyurethane-34, VP/polycarbamyl polyglycol ester, or combinations thereof; a skin adhesion promoter comprising polydiethyleneglycol adipate/isophorone diisocyanate copolymer, Polyester-7 (and) neopentylglycol polyester, VP/eicosene copolymer, hydrogenated polyisobutene (and) butylene/ethylene/styrene copolymer (and) ethylene/propylene/styrene copolymer, bis-PPG-15 dimethicone/IPDI copolymer, Polyurethane-18, or combinations thereof; a color enhancer comprising silicone resins, silicone cross-polymers, silicone copolymers, silicone elastomers, silicone resin elastomer gels, silica, fumed silica, amorphous silica, silica dimethyl silylates, hydrophobic modified silica, hydrated silica, silicates, or combinations thereof; and one or more colorants.

The inventive compositions of the present invention can be formulated as a lotion, cream gel, or spray. A self-tanner may also be formulated therein.

DETAILED DESCRIPTION OF THE INVENTION

In the following description of the present invention and the claims appended hereto, it is to be understood that all concentrations are by weight percent based on a total weight of the composition unless otherwise indicated. Where appropriate, the INCI (international Nomenclature of Cosmetic Ingredients) name of ingredients/components is used.

The present invention is directed to a multi-functional cosmetic composition having an improved skin feel and appearance with good color intensity and color retention even after water exposure. The composition comprises the following components: a film former, a skin adhesion promoter, a color enhancer, and one or more colorants. It may further comprise a variety of different actives to provide desired functionality to the user. The unexpected synergy of the individual components together preserves color intensity and color retention even after water exposure so that skin appearance is continually enhanced. The cosmetic compositions of the present invention have the advantage of being durable, transfer-resistant, water resistant, color intense, and comfortable to the wearer. The cosmetic compositions can be formulated with pharmaceutically acceptable carrier components to provide different formulations as a lotion, cream gel, or spray.

The film formers useful in the present invention protect the active ingredients and colorants from being removed from the skin by mechanical forces, i.e., rubbing. They also contribute to the water resistance of the final composition such that the actives and colorants are not easily washed off. In sunscreen compositions, the film formers are an important component to substantiate the claim of water resistance.

Film formers useful in the present invention may comprise one or more polymers. The following are examples of suitable polymers, but the list is by no means limiting. Film former polymers may include acrylate copolymers such as those obtained by emulsion polymerization, and more specifically, acrylate/$C_{12-22}$ methacrylate copolymer polymerized from monomers of methacrylic acid, methyl methacrylate, butyl acrylate, and cetyl-eicosinyl methacrylate; and PPG-17/isophorone diisocyanate (IPDI)/dimethylol propionic acid (DMPA) copolymer. There are also aqueous polyurethane polymer dispersions such as Polyurethane-34 which is a sodium salt of polymerized monomers of adipic acid, 1,6-hexandiol, neopentyl glycol, hexamethylene diisocyanate, ethylene diamine, N-(2-aminoethyl)-3-aminoethanesulphonic acid; Polyurethane-32 which is a sodium salt of polymerized monomers of polytetramethylene glycol, hexamethylene diisocyanate, (IPDI), ethylene diamine, N-(2-aminoethyl)-3-aminoethanesulphonic acid; Polyurethane-35 which is a sodium salt of polymerized monomers of adipic acid, 1,6-hexandiol, neopentyl glycol, dicyclohexylmethane diisocyanate, ethylene diamine, N-(2-aminoethyl)-3-aminoethanesulphonic acid; and Polyurethane-48 which is a sodium salt of polymerized monomers of adipic acid, 1,6-hexandiol, neopentyl glycol, isophorone diisocyanate, isophorone diamine, N-(2-aminoethyl)-3-aminoethanesulphonic acid. Also useful are vinylpyrrolidone (VP) and polyvinylpyrrolidone (PVP) crosspolymers, copolymers and/or interpolymers such as hydrolyzed wheat protein/PVP crosspolymers; maltodextrin/VP copolymer; butylated/PVP copolymer; VP/polycarbamylpolyglycol ester; VP/dimethylaminoethylmethacrylate/polycarbamyl polyglycol ester; and VP/dimethiconyl-acrylate/polycarbamyl polyglycol ester. One of skill in the art will understand that the above film formers may be used in combination to achieve the desired properties of the final cosmetic composition.

In most preferred embodiments, the film former comprises acrylate/$C_{12-22}$ methacrylate copolymer; PPG-17/IPDI/DMPA copolymer; Polyurethane-34; VP/polycarbamyl polyglycol ester; or combinations thereof.

These preferred film formers are commercially available as ALLIANZ® OPT available from Ashland Inc.; SOL- TEX® OPT PG available from Dow Chemical Company; AVALURE® UR 450 available from Lubrizol Corp.; POLYDERM® PPG-17 available from Alzo International Inc.; BAYCUSAN® available from Bayer Material Science LLC; and PECOGEL® available from Phoenix Chemical, Inc.

The film former is present in the cosmetic composition in an amount of at least about 0.01 to about 30.0 wt. %, based on a total weight of the cosmetic composition. Preferably, the film former is present in an amount of about 0.1 to about 10.0 wt. %, based on a total weight of the cosmetic composition. In a most preferred embodiment, the film former is present in an amount of about 0.5 to about 3.0 wt. %, based on a total weight of the cosmetic composition.

The cosmetic compositions of the present invention further include a skin adhesion promoter that may comprise one or more polymers. The skin adhesion promoter theoretically entraps the active ingredients within its polymeric network to prevent the actives from migrating. It can also act as a plasticizer to soften the film former and works synergistically with the film forming component to enhance the water resistance of the final cosmetic composition. Depending upon the other components of the formulation, the skin adhesion promoter may be hydrophobic, hydrophilic, or a combination of both. One of skill in the art will understand that the foregoing skin adhesion promoters may be used in combination to achieve the desired properties of the final cosmetic composition.

Hydrophobic skin adhesion promoter polymers useful in the present invention may include, but are not limited to, copolymers of monomers of a fatty acid and IPDI. Examples of such copolymers include polydiethylene glycol adipate/IPDI copolymer; hydrogenated castor Oil/IPDI copolymer; polyglyceryl-2 diisostearate/IPDI copolymer; glyceryl diricinoleate/IPDI copolymer; propylene glycol diricinoleate/IPDI copolymer; dimethiconol/IPDI copolymer (and) cyclomethicone; bis-PPG-15 dimethicone/IPDI copolymer. A useful saturated methylene diphenyldiisocyanate (SMDI) copolymer may be PPG-12/SMDI copolymer. Particular crosspolymers of adipic acid monomers are also useful. Exemplary of those crosspolymers of adipic acid monomers are adipic acid/diglycol crosspolymer; and trimethylpentanediol/adipic acid/glycerin crosspolymer. The hydrophobic skin adhesion promoters may also comprise polyesters such as Polyester-10 combined with propylene glycol dibenzoate as an emollient (herein referred to as Polyester-10 (and) propylene glycol dibenzoate), or Polyester-7 combined with neopentyl glycol polyester as an emollient (herein referred to as Polyester-7 (and) neopentylglycol polyester). Other copolymers useful as skin adhesion promoters may be VP or PVP copolymers such as VP/hexadecene copolymer, VP/eicosene copolymer, and tricontanyl PVP; (meth)acrylate copolymers such as acrylic acid/isobornylmethacrylate/isobutylmethacrylate copolymer/isododecane in isododecane, or behenyl methacrylate/t-butyl methacrylate copolymer; or hydrogenated olefinic polymers such as hydrogenated polyisobutene and copolymers thereof; or hydrogenated polycyclopentadiene. Gel polymers such as petrolatum (and) ethylene/propylene/styrene copolymer, butylene/ethylene/styrene copolymer are also contemplated herein.

Preferred hydrophobic skin adhesion promoter polymers comprise polydiethylene glycol adipate/IPDI copolymer available as POLYDERM® PPI-PE from Alzo International Inc.; Polyester-7 (and) neopentylglycol polyester which is available as LEXFILM® Sun from Inolex Chemical Company; VP/eicosene copolymer available as GANEX®/ANTARON® V-220/V-220F from Ashland Inc.; hydrogenated polyisobutene (and) butylene/ethylene/styrene copolymer (and) ethylene/propylene/styrene copolymer available as PARLEAM® Gel from NOF Corp, individually or combinations thereof.

Hydrophilic skin adhesion promoters useful in the present invention may be selected from, but are not limited to, the following IPDI copolymers such as PEG-40 hydrogenated castor oil/IPDI copolymer; PEG-200 hydrogenated castor oil/IPDI copolymer; glycereth-7/hydroxystearate/IPDI copolymer; bis-PPG-15 dimethicone/IPDI copolymer; and Polyurethane-18; individually or combinations thereof.

Preferred hydrophilic skin adhesion promoter polymers are bis-PPG-15 dimethicone/IPDI copolymer available as POLYDERM® PPI-SI-WS from Alzo International Inc.; and Polyurethane-18 available as POLYDERM PE/PA also from Alzo International.

Preferably, the skin adhesion promoter is present in a weight ratio of skin adhesion promoter to the photoactives of the cosmetic composition from about 1:150 to about 1:0.1, and preferably in a weight ratio of about 1:80 to about 1:1. Alternatively, the skin adhesion promoter is present in an amount of about 0.05 to about 15.0 wt. %, more preferably in an amount of about 0.1 to about 7.0 wt. %, and most preferably in an amount of about 0.1 to about 3.0 wt. %, all based on a total weight of the composition.

The cosmetic compositions of the present invention further comprise a color enhancer. The color enhancer promotes uniform distribution of the colorants in the cosmetic composition for improved color intensity, and prevents the colorants from rubbing or transferring off the skin onto clothing and other substrates. It provides enhanced wetting of the colorants within the cosmetic formulation. It is preferred that the color enhancer comprises a material containing silicon.

Such silicon-based color enhancers of the present invention are preferably selected from, but are not limited to, silicone resins, silicone crosspolymers, silicone copolymers, silicone elastomers, silicone resin elastomer gels, silica, fumed silica, amorphous silica, silica dimethyl silylates, hydrophobic modified silica, hydrated silica, silicates, and combinations thereof. Preferred color enhancers useful in the present invention comprise copolymers or crosspolymers of trimethylsiloxysilicate such as trimethylsiloxysilicate/polypropylsilsesquioxane copolymer; polymethylsilsesquioxane; polyphenylsilsesquioxane; $C_{30-45}$ alkyl dimethylsilyl polypropylsilsesquioxane. Dimethicone copolymers or crosspolymers such as dimethicone (and) polysilicone-11 crosspolymer; dimethicone (and) cetearyl dimethicone crosspolymer; dimethicone (and) dimethicone crosspolymer; stearoxymethicone/dimethicone copolymer; and/or dimethicone (and) vinyldimethyl/trimethylsiloxysilicate/dimethicone crosspolymer are all contemplated. Silicas useful as color enhancers include, but are not limited to, hydrated silica, fumed silica, pyrogenic silica, and/or hydrophobic modified silica. Kaolin may also be used a color enhancer as well. One of skill in the art knows that one or more color enhancers may be needed to formulate the desired properties of the final cosmetic composition.

Preferred color enhancers are trimethylsiloxysilicate available as BELSIL® from Wacker Chemie AG, or the MQ line of resins by Dow Corning, as well as other suppliers; trimethylsiloxysilicate (and) polypropylsilsesquioxane, another MQ resin from Dow Corning; dimethicone (and) polysilicone-11 available as GRANSIL® DMG-3 from Grant Industries Inc. Preferred silicas are available as CAB-O-SIL® from Cabot Corp. or SYLOID® from WR Grace & Company.

The color enhancers are preferably present in the cosmetic composition of the present invention in a weight ratio of color enhancer to colorants ranging from about 1:50 to about 1:0.05. Preferably, the weight ratio of color enhancer to colorants ranges from about 1:10 to about 1:0.1, and most preferably, the weight ratio ranges from about 1:4 to about 1:0.4. Alternatively, the color enhancer is preferably present in an amount of about 0.01 wt. % to about 10.0 wt. %, more preferably from about 0.05 wt. % to about 10.0 wt. %, and most preferably from about 0.05 wt. % to about 2.5 wt. %.

Colorants provide a variety of color to the cosmetic compositions of the present invention to further enhance skin appearance. Such colorants are known to one of skill in the art, particularly in the cosmetic composition field, and may include, but are not limited to, hennas, caramels, malva extracts, hibiscus extracts, tyrosines, green teas, glyceraldehydes, ginsengs, erythruloses, ferric compounds (including iron oxide), annattos, ultramarine pigments, beta-carotenes, carmines, chrome oxides, titanium oxide, zinc oxide, D&C water-soluble dyes, bismuth compounds, FD&C water-soluble dyes, copper powders, guanines, walnut extracts, iron oxides, micas, and combinations thereof. Hennas, caramels, micas, pearl pigments, pearlescent pigments, or combinations thereof, are preferred.

Pearlescent pigments are most preferred, and can be selected from white pearlescent pigments, such as mica covered with titanium or with bismuth oxychloride; colored pearlescent pigments, such as titanium oxide-coated mica with iron oxides, titanium oxide-coated mica with ferric blue or chromium oxide; or titanium oxide-coated mica with an organic pigment of the abovementioned type, and pearlescent pigments based on bismuth oxychloride.

The colorants are present in the cosmetic compositions of the present invention from about 0.01 wt. % to about 20.0 wt, %, preferably from about 0.05 wt. % to about 10.0 wt. %, more preferably from about 0.05 wt. % to about 2.5 wt. %, and most preferably from about 0.1 wt. % to about 1.5 wt. %, of these skin coloring agents, all based on a total weight of the composition.

The cosmetic compositions of the present invention may optionally include other active or inactive ingredients such as those selected from, but not limited to, cosmetically acceptable carriers, oils, sterols, amino acids, moisturizers, powders, ultraviolet absorbents or photoactives, colorants (including pigments and/or dyes) pH adjusters, perfumes, essential oils, cosmetic active ingredients, vitamins, essential fatty acids, sphingolipids, self-tanning compounds such as dihydroxyacetone (DHA) and erythruloses, sunscreens, excipients, fillers, emulsifying agents, antioxidants, surfactants, film formers, chelating agents, gelling agents, thickeners, emollients, humectants, moisturizers, minerals, viscosity and/or rheology modifiers, keratolytics, retinoids, hormonal compounds, alpha-hydroxy acids, alpha-keto acids, anti-mycobacterial agents, anti-fungal agents, antimicrobials, anti-virals, analgesics, anti-allergenic agents, H1 or H2 antihistamines, anti-inflammatory agents, anti-irritants, anti-neoplastics, immune system boosting agents, immune system suppressing agents, anti-acne agents, anesthetics, antiseptics, insect repellents, skin cooling compounds, skin protectants, skin penetration enhancers, exfoliants, lubricants, fragrances, colorants, staining agents, depigmenting agents, hypopigmenting agents, preservatives, stabilizers, pharmaceutical agents, photostabilizing agents, spherical powders and mixtures thereof.

The cosmetic compositions of the present invention may also have other optional additives. For instance, one or more fragrances; plant extracts; absorbents; thickeners/rheology modifiers; salicylic acid; alpha and beta hydroxy acids; vitamins including vitamins A, C, and E; retinol and its derivatives; preservatives; or any mixtures thereof, may be included in the cosmetic compositions.

Exemplary embodiments of the cosmetic compositions of the present invention may comprise about 0.01 wt. % to about 30.0 wt. %. of the water dispersible film former; about 0.05 wt. % to about 15.0 wt. % of the skin adhesion promoter; about 0.01 wt. % to about 20 wt. % colorants; and the color enhancer to colorants weight ratio is about 1:50 to about 1:0.05, based on a total weight of the composition.

Another exemplary embodiment of the cosmetic composition of the present invention may comprise about 0.1 wt. % to about 10.0 wt. % of the water dispersible film former; about 0.05 wt, % to about 7.0 wt. % of the skin adhesion promoter; about 0.1 wt, % to about 5.0 wt. % colorants; and the color enhancer to colorants weight ratio is about 1:10 to about 1:0.1, based on a total weight of the composition.

Yet another exemplary embodiment of the cosmetic composition of the present invention may comprise about 0.5 wt. % to about 3.0 wt. % of the film former; about 0.1 wt. % to about 3.0 wt. % of the skin adhesion promoter; about 0.1 wt. % to about 5.0 wt. % colorants; and the color enhancer to colorants weight ratio is about 1:4 to about 1:0.4, based on a total weight of the composition.

In a most preferred embodiment, the cosmetic compositions of the present invention comprise sunscreen compositions by incorporating one or more photoactive agents into the composition. The one or more photoactives that can be used in the present invention must be capable of absorbing or blocking the harmful effects of ultraviolet radiation. In addition, they must be non-toxic and non-irritating when applied to the skin. Suitable photoactives that may be used in the sunscreen composition include, but are not limited to p-aminobenzoic acid and derivatives thereof; butyl methoxydibenzoylmethane; benzophenones; hydroxy-substituted benzophenones; methoxy-substituted benzophenones; benzophonone-1; benzophenone-2; benzophenone-3; benzophenone-4; benzophenone-6; benzophenone-8; benzophenone-12; methoxycinnamate; ethyl dihydroxypropyl-p-aminobenzoate; glyceryl-p-aminobenzoate; homosalate; methyl anthranilate; octocrylene; octyl dimethyl-p-aminobenzoate; octyl methoxycinnamate; octyl salicylate; 2 phenylbenzimidazole-5-sulphonic acid; triethanolamine salicylate; 3-(4-methylbenzylidene)-camphor; red petrolatum, 3-(4-methylbenzyldine)boran-2-one(methylbenzindinecamphor); benzotriazole; salicylates; phenylbenzimidazole-5-sulfonic acid; methylene bis-benzotriazolyl tetramethylbutyl phenol; avobenzone; 4-isopropyldibenzoylmethane; butyl-methoxydibenzoylmethane; octisalate; oxybenzone; bis-ethylhexyloxyphenol methoxy triazine; 4-isopropyl-dibenzoyl-methane; metal oxides; zinc oxide; octyltriethoxy silanol; titanium dioxide; alumina; triethoxy silane; and combinations thereof.

The preferred sunscreen agents are avobenzone, benzophenone-3, octyl methoxycinnamate, octyl salicylate, homosalate, zinc oxide, octocrylene, titanium dioxide, or combinations thereof. The one or more sunscreen agents are included in a present composition at about 1.0 wt. % to about 40.0 wt. % based on a total weight of the composition. The amount and types of photoactives in the composition will vary in the above range depending on the sun protection factor (SPF) desired. The higher the SPF, the greater the total amount of photoactives. Preferably, the one or more photoactives are present in an amount of about 1 wt. % to about 35 wt. % to achieve a SPF of about 2 to about 50.

In one embodiment of the present invention, the cosmetic composition includes about 0.1 wt. % to about 10.0 wt. % of one or more film formers selected from the group consisting of acrylate/$C_{12-22}$ methacrylate copolymer, PPG-17/IPDI/DMPA copolymer, Polyurethane-34, VP/carbamyl polyglycol ester, and combinations thereof; about 0.05 wt. % to about 15.0 wt. % of one or more skin adhesion promoters selected from the group consisting of polydiethylene glycol adipate/IPDI copolymer, Polyester-7 (and) neopentylglycol polyester, VP/eicosene copolymer, hydrogenated polyisobutene (and) butylene/ethylene/styrene copolymer (and) ethylene/propylene/styrene copolymer, bis-PPG-15 dimethicone/IPDI, Polyurethane-18, and combinations thereof; about 0.2 wt. % to about 2.5 wt. % of one or more color enhancers selected from the group consisting of trimethylsiloxysilicate, trimethylsiloxysilicate (and) polypropylsilsesquioxane resin, dimethicone (and) polysilicone-11, fumed silica, hydrated silica, and combinations thereof; and one or more colorants, wherein said composition is very water resistant for up to 80 minutes.

In another embodiment of the present invention, the cosmetic composition is a sunscreen composition having an SPF of 4 comprising about 1.0 wt. % to about 3.0 wt. % of a film former; about 0.05 wt. % to about 1.0 wt. % of a skin adhesion promoter; about 0.2 wt. % to about 2.5 wt. % of a color enhancer; and about 2.0 wt. % of one or more photoactive agent. Preferably, the photoactives comprise octisalate, octocrylene, and avobenzone.

In yet another embodiment of the present invention, the cosmetic composition is a sunscreen composition having an SPF of 8 comprising 1.0 wt. % to about 3.0 wt. % of a film former; about 0.05 wt. % to about 1.0 wt. % of a skin adhesion promoter; about 0.2 wt. % to about 2.5 wt. % of a color enhancer; and about 5.0 wt. % of one or more photoactive agents. Preferably, the photoactives comprise octisalate, octocrylene, and avobenzone.

In yet another embodiment of the present invention, the cosmetic composition is a sunscreen composition having an SPF of 15 comprising 1.0 wt. % to about 3.0 wt. % of a film former; about 0.05 wt. % to about 1.0 wt. % of a skin adhesion promoter; about 0.2 wt. % to about 2.5 wt. % of a color enhancer; and about 8.0 wt. % of one or more photoactives. Preferably, the photoactives comprise octisalate, octocrylene, and avobenzone.

In a particular embodiment of the present invention, the cosmetic composition is a sunscreen composition having an SPF of 30 comprising 1.0 wt. % to about 3.0 wt. % of a film former; about 0.05 wt. % to about 1.0 wt. % of a skin adhesion promoter; about 0.2 wt. % to about 2.5 wt. % of a color enhancer; and about 13.0 wt. % of one or more photoactives. Preferably, the photoactives comprise homosalate, octisalate, octocrylene, and avobenzone.

One or more colorants may be included in the preceding sunscreen compositions in an amount of about 0.1 wt. % to about 5.0 wt. %. Self-tanners may also be incorporated as well.

The cosmetic compositions may be prepared by using techniques and methods well known in the art. In general, all water soluble ingredients are placed in a main vessel such as thickeners, chelating agents, humectants, pH adjusters, water dispersible film formers, hydrophilic skin adhesion promoters, and/or water soluble actives. This water phase is mixed until uniform and heated to about 80° C. In a separate vessel, the oil soluble ingredients such as solvents, emollients, emulsifiers, emulsion stabilizers, preservatives, hydrophobic skin adhesion promoters, and/or oil soluble actives, including photoactives, are mixed until uniform and heated to about 80° C. The oil phase is added to the water phase, homogenized for 5 minutes until uniform, and the resultant mixture is cooled to room temperature. During the cooling period, the remaining ingredients are admixed therein. Any ingredients that are heat sensitive are added at this point.

The cosmetic compositions of the present invention can then be formulated and packaged as a lotion, cream gel, spray, including alcohol-based sprays, or other acceptable carriers suitable for a cosmetic composition, in particular, a sunscreen composition.

The following testing of inventive formulations and comparative formulations unexpectedly show that the synergistic effects of the water dispersible film former, skin adhesion promoters, and color enhancers work together to improve the color intensity and color retention of the cosmetic compositions of the present invention.

An initial color reading of a subject's forearm skin was measured using a Konica Spectrophotometer CM-2600D with three sensors represented by numerical values plotted in a colorspace characterized by the brightness, L*, and the color coordinates a* and b*, as defined by the International Lighting Commission (Commission Internationale de l'Eclairage, or CIE) (1976). This initial reading is the baseline for each subject.

Twenty-five milligrams of each sample was lightly spread within a 4 cm diameter circular test area on the subject's forearms. The sample was allowed to dry on the skin for 5 minutes. A second reading, $\Delta E1$, was taken, representing the color difference between the baseline and after application of the sample. Samples showing good color intensity after application are marked with a positive sign "+." Raw data was statistically analyzed using the Student t-test.

Thereafter, the test area was subjected to a wet-rub method to evaluate the color retention of the samples on human skin after water exposure. This method simulates the effect of exposing the application area to water. After the initial application was dried, about 250 ml of tap water was used to completely wet the test area. A paper towel was placed on the top of the wet test area and a paint roller (6 inch×¾ inch nap) pre-wrapped with two pounds of waist/angle weight was rolled over the top of the paper towel to create friction between the forearm test area and the paper towel. After rolling back and forth 20 times, a third reading, $\Delta E2$, was taken thereafter representing the difference in color between the initial application and after the wet-rub. Samples showing good color retention, when compared with the color intensity after the initial application and after the wet rub, are marked with a positive sign "+." Raw data was statistically analyzed using the Student t-test.

A lotion, Base Formula A, was prepared using methods known to one of skill in the art in formulating cosmetic compositions. Components of Base Formula A are listed in Table I below. Samples were prepared and tested with individual components of the cosmetic composition of the present invention and then compared with a cosmetic composition of the present invention highlighting the synergistic effect when the film former, skin adhesion promoter, and color enhancer are present in the same composition.

TABLE I

Base Formula A - Lotion

| Component | wt. %* |
|---|---|
| Deionized Water | QS. to 100 |
| Acrylates/$C_{10-30}$ alkyl acrylate crosspolymer | 0.2-0.4 |

TABLE I-continued

Base Formula A - Lotion

| Component | wt. %* |
|---|---|
| Disodium EDTA | 0.05-0.2 |
| Glycerin | 1.0-4.0 |
| Sodium Hydroxide | 0.08-0.2 |
| Diisopropyl adipate | 1.0-3.0 |
| Polyglyceryl-3 methylglucose distearate | 1.0-3.0 |
| Glyceryl stearate and PEG-100 stearate | 0.5-2.0 |
| Cetyl alcohol | 0.1-2.0 |
| Butters | 0.1-1.0 |
| Octocrylene | 1.0 |
| Avobenzone | 0.5 |
| Caramel and Pearls | 0.1-5.0 |
| Phenoxyethanol, methyl and propyl parabens | 0.3-1.5 |
| Vitamins | 0.01-0.1 |
| Botanical extracts and powders | 0.1-2.0 |
| Fragrance | 0.25 |

*based on a total weight of the composition

As shown in Table II, Samples 1 to 6 were prepared using Base Formula A as a base composition, and incorporating one or more of the individual components of the cosmetic composition of the present invention. Sample 7 is a composition of the present invention which demonstrates the unexpected synergy of the film former, skin adhesion promoter, and color enhancer when used concurrently in the base formulation.

TABLE II

Lotion Samples

| Sample # | Components |
|---|---|
| 1 | Base Formula A<br>+6 wt. % snow white petrolatum USP |
| 2 | Base Formula A<br>+6 wt. % snow white petrolatum USP<br>+7 wt. % acrylates/$C_{12-22}$ methacrylate copolymer |
| 3 | Base Formula A<br>+6 wt. % snow white petrolatum USP<br>+7 wt. % polydiethyleneglycol adipate/IPDI copolymer |
| 4 | Base Formula A<br>+6 wt. % snow white petrolatum USP<br>+7 wt. % trimethylsiloxysilicate (CE) |
| 5 | Base Formula A<br>+6 wt. % snow white petrolatum USP<br>+3.5 wt. % acrylates/$C_{12-22}$ methacrylate copolymer<br>+3.5 wt. % trimethylsilosilicate |
| 6 | Base Formula A<br>+6 wt. % snow white petrolatum USP<br>+3.5 wt. % acrylates/$C_{12-22}$ methacrylate copolymer<br>+3.5 wt. % polydiethyleneglycol adipate/IPDI copolymer |
| 7 | Base Formula A<br>+6 wt. % snow white petrolatum USP<br>+3.5 wt. % acrylates/$C_{12-22}$ methacrylate copolymer<br>+2.5 wt. % trimethylsilosiliate<br>+1 wt. % polydiethyleneglycol adipate/IPDI copolymer |

Water resistance testing was conducted in accordance with 21 C.F.R. § 352.72(a). Samples 1 to 7 met or exceeded the 2011 U.S. Food & Drug Administration (FDA) water resistance guidelines for 80 minutes.

Base Formula A lotion, the control, which did not contain any film formers, skin adhesion promoters, color enhancers, showed both poor initial color intensity and subsequently poor color retention after the wet rub. Samples 1, 3, 4 and 6 did not show significant improvement in skin color and color retention in comparison to the control. Samples 2 and 5 did not show significant improvement in color intensity, but did show significant improvement on color retention after wet rub in comparison to the control. Only Sample 7, the inventive composition, showed statistically significant improvements in both color intensity and color retention when compared to the performance of the control.

| Sample # | ΔE1 | ΔE2 | % Color Retention |
|---|---|---|---|
| Base Formula A | – | – | 72 |
| 1 | – | – | 69 |
| 2 | – | – | 94 |
| 3 | – | – | 59 |
| 4 | – | – | 83 |
| 5 | – | – | 88 |
| 6 | – | – | 75 |
| 7* | + | + | 87 |

*$p < 0.05$ by Student t-test

A second formulation, Base Formula B, was prepared using methods known to one of skill in the art in formulating cosmetic compositions. Components of Base Formula B, a low viscosity spray lotion, are listed in Table III below. Samples were prepared with individual components of the cosmetic composition of the present invention and then compared with a cosmetic composition of the present invention highlighting the synergistic effect when the film former, skin adhesion promoter, and color enhancer are present in the same composition.

TABLE III

Base Formula B - Low Viscosity Spray Lotion

| Component | wt. %* |
|---|---|
| Deionized Water | QS. to 100 |
| Xanthan Gum | 0.1-1.0 |
| Orange Fiber | 0.3-1.0 |
| Disodium EDTA | 0.05-0.2 |
| Glycerin | 0.5-4.0 |
| Sodium Hydroxide | 0.01-0.2 |
| Diisopropyl adipate | 1.0-3.0 |
| Polyglyceryl-3 methylglucose distearate | 1.0-3.0 |
| Glyceryl stearate and PEG-100 stearate | 0.5-2.0 |
| Cetyl alcohol | 0.1-2.0 |
| Octisalate | 2.0 |
| Octocrylene | 1.4 |
| Avobenzone | 1.2 |
| Caramel and Pearls | 0.1-5.0 |
| Phenoxyethanol, Methyl and Propyl parabens | 0.5-1.6 |
| Cocoa powders | 0.1-2.0 |
| Fragrance | 0.25 |

*based on a total weight of the composition

As shown in Table IV, Samples 8 and 9 were prepared using Base Formula B and incorporating one or more of the individual components of the cosmetic composition of the present invention. Sample 10 is a composition of the present invention which shows the unexpected synergy of the film former, skin adhesion promoter, and color enhancer when used concurrently in the base formulation.

TABLE IV

Spray Lotion Samples

| Sample # | Components |
|---|---|
| 8 | Base Formula B<br>+7 wt. % VP/eicosene copolymer |
| 9 | Base Formula B<br>+7 wt. % PPG-17/IPDI/DMPA copolymer |

TABLE IV-continued

Spray Lotion Samples

| Sample # | Components |
|---|---|
| 10 | Base Formula B |
| | +3.5 wt. % acrylates/$C_{12-22}$ methacrylate copolymer |
| | +2.5 wt. % trimethylsilosiliate |
| | +1 wt. % polydiethyleneglycol adipate/IPDI copolymer |

Water resistance testing was conducted in accordance with 21 C.F.R. § 352.72(a). Sample 10 met or exceeded the 2011 U.S. Food & Drug Administration (FDA) water resistance guidelines for 80 minutes.

| Sample # | ΔE1 | ΔE2 | % Color Retention |
|---|---|---|---|
| 8 | – | – | 87 |
| 9 | – | – | 80 |
| 10* | – | + | 99 |

*$p < 0.01$ by Student t-test

Sample 10, the inventive composition, unexpectedly showed significant improvements in initial color intensity and color retention after wet rub than both Samples 8 and 9.

A third formulation Base Formula, C, was prepared using methods known to one of skill in the art in formulating cosmetic compositions. Components of Base Formula C, a cream gel, are listed in Table V below. Samples were prepared with individual components of the cosmetic composition of the present invention and then compared with a cosmetic composition of the present invention highlighting the synergistic effect when the film former, skin adhesion promoter, and color enhancer are present in the same composition.

TABLE V

Base Formula C - Cream Gel

| Components | wt. %* |
|---|---|
| Deionized Water | QS. to 100 |
| Acrylates/$C_{10-30}$ Alkyl acrylate crosspolymer | 0.5-1.5 |
| Hydroxyethylcellulose | 0.1-1.0 |
| Disodium EDTA | 0.05-0.2 |
| Glycerin | 0.5-4.0 |
| Water, Glycerin, Glyceryl Acrylate/Acrylic acid copolymer, Propylene glycol (and) PVM/MA copolymer | 1.0-5.0 |
| Aminomethylpropanol and water | 0.5-1.0 |
| Polyglyceryl-4 laurate/Sebacate (and) Polyglyceryl-6 caprylate/Caprate (and) water | 4.0-8.0 |
| Octisalate | 2.0 |
| Octocrylene | 1.4 |
| Avobenzone | 1.2 |
| Caramel and Pearls | 0.1-5.0 |
| Phenoxyethanol and Ethylhexyl glycerin | 1.0-2.0 |

*based on a total weight of the composition

As shown in Table VI, Samples 11 was prepared using Base Formula C as a cream gel and incorporating only a skin adhesion promoter. Sample 12 is a composition of the present invention which shows the unexpected synergy of the film former, skin adhesion promoter, and color enhancer when used concurrently in the base formulation.

TABLE VI

Cream Gel Samples

| Sample # | Components |
|---|---|
| 11 | Base Formula C |
| | +7 wt. % bis-PEG-15 dimethicone/IPDI copolymer |
| 12 | Base Formula C |
| | +3.5 wt. % acrylates/$C_{12-22}$ methacrylate copolymer |
| | +2.5 wt. % trimethylsilosiliate |
| | +1 wt. % polydiethyleneglycol adipate/IPDI copolymer |

Sample 12, an inventive composition, showed statistically significant improvement in overall color intensity when compared to Sample 11.

| Sample # | ΔE1 | ΔE2 | % Color Retention |
|---|---|---|---|
| 11 | – | – | 53 |
| 12* | – | + | 86* |

$p < 0.05$ by Student t-test

To further evaluate the inventive composition of the present inventions, a low viscosity formulation of the present invention that includes the film former, skin adhesion promoter and color enhancer, similar to sample 10, was also evaluated by consumers for a two week period using the home-use test. In a total of 156 consumers, over 70% of respondents agreed that the inventive formulation enhanced their appearance such as providing a bronzed look, a beautiful sheen to their skin, natural looking color, as well as streak-free color. At least 73% of respondents agreed that the color did not rub off on their clothes. Over 75% of respondents agreed that this particular formulation felt good on the skin, did not leave the skin feeling greasy, and helped even out the skin tone.

The above invention achieves the objects recited above. Inventive compositions of the present invention comprising a film former, skin adhesion promoter, and color enhancer are water resistant, and unexpectedly provide improved color intensity and color retention, with a non-greasy skin feel and appearance.

While the present invention has been particularly described, in conjunction with specific preferred embodiments, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:
1. A cosmetic composition consisting essentially of:
one or more photoactives;
a water dispersible film former component, present in an amount of 0.5 wt. % to 10.0 wt. % based on a total weight of said composition, selected from the group consisting of acrylate/$C_{12-22}$ methacrylate copolymer, polypropylene glycol (PPG)-17/isophorone diisocyanate (IPDI)/dimethylol propionic acid (DMPA) copolymer, hydrolyzed wheat protein/polyvinyl pyrrolidone crosspolymer, maltodextrin/vinyl pyrrolidone (VP) copolymer, butylated/polyvinyl pyrrolidone copolymer, VP/polycarbamyl polyglycol ester, VP/dimethylaminoethyl methacrylate/polycarbamyl polyglycol ester, and/or VP/dimethiconyl-acrylate/polycarbamyl polyglycol ester;

a skin adhesion promoter component, present in an amount of about 0.05 wt. % to about 15.0 wt. % based on a total weight of said composition, comprising polyethylene glycol (PEG)-40 hydrogenated castor oil/IPDI copolymer, PEG-200/hydrogenated castor oil/IPDI copolymer, and/or glycereth-7/hydroxystearate/IPDI copolymer, wherein a weight ratio of said skin adhesion promoter to said photoactives is 1:80 to 1:1;

a color enhancer component comprising one or more silicon materials; and one or more colorants.

2. The cosmetic composition of claim 1, wherein said water dispersible film formers is acrylate/$C_{12-22}$ methacrylate copolymer, PPG-17/IPDI/DMPA copolymer, and/or VP/polycarbamyl polyglycol ester.

3. The cosmetic composition of claim 1, wherein said water dispersible film former is acrylate/$C_{12-22}$ methacrylate copolymer.

4. The cosmetic composition of claim 1, wherein said skin adhesion promoter further comprises bis-PPG-15 dimethicone/IPDI copolymer.

5. The cosmetic composition of claim 1, wherein said skin adhesion promoter further comprises a mixture of polyester-7 and neopentylglycol polyester, VP/eicosene copolymer, a mixture of hydrogenated polyisobutene, butylene/ethylene/styrene copolymer, and ethylene/propylene/styrene copolymer, bis-PPG-15 dimethicone/IPDI copolymer, and/or polydiethylene glycol adipate/IPDI copolymer.

6. The cosmetic composition of claim 1, wherein said skin adhesion promoter is present in an amount of about 0.1 wt. % to about 7.0 wt. % based on a total weight of the composition.

7. The cosmetic composition of claim 1, wherein the silicon material is selected from the group consisting of silicone resins, silicone cross-polymers, silicone copolymers, silicone elastomers, silicone resin elastomer gels, silica, fumed silica, amorphous silica, silica dimethyl sylilates, hydrophobic modified silica, and/or hydrated silica.

8. The cosmetic composition of claim 7, wherein the silicone resins comprise trimethylsiloxysilicate/polypropylsilsesquioxane silicone resin, polymethylsilsesquioxane, polyphenylsilsesquioxane, $C_{30-45}$ alkyl dimethylsilyl polypropylsilsesquioxane, a mixture of dimethicone and polysilicone-11 crosspolymer, a mixture of dimethicone and cetearyl dimethicone crosspolymer, a mixture of dimethicone and dimethicone crosspolymer, stearoxymethicone/dimethicone copolymer, and/or a mixture of dimethicone and vinyldimethyl/trimethylsiloxysilicate/dimethicone crosspolymer.

9. The cosmetic composition of claim 7, wherein the silica is selected from hydrated silica, fumed silica, pyrogenic silica, and/or hydrophobic modified silica.

10. The cosmetic composition of claim 1, wherein a weight ratio of said color enhancer to said one or more colorants is about 1:50 to about 1:0.05.

11. The cosmetic composition of claim 1, wherein said one or more colorants comprise hennas, caramels, malva extracts, hibiscus extracts, tyrosines, green teas, glyceraldehydes, ginsengs, erythruloses, iron oxides, annattos, ultramarine pigments, beta-carotenes, carmines, chrome oxides, titanium oxide, zinc oxide, bismuth compounds, water-soluble dyes, copper powders, guanines, walnut extracts, and/or micas.

12. The cosmetic composition of claim 1, wherein said one or more colorant comprises hennas, caramels, micas, pearl pigments, and/or pearlescent pigments.

13. The cosmetic composition of claim 1, wherein said one or more photoactives selected from the group consisting of p-aminobenzoic acid and derivatives thereof, butyl methoxydibenzoylmethane, benzophenones, hydroxy-substituted benzophenones, methoxy-substituted benzophenones, benzophenone-1, benzophenone-2, benzophenone-3, benzophenone-4, benzophenone-6, benzophenone-8, benzophenone-12, methoxycinnamate, ethyl dihydroxypropyl-p-aminobenzoate, glyceryl-p-aminobenzoate, homosalate; methyl anthranilate, octocrylene, octyl dimethyl-p-aminobenzoate, octyl methoxycinnamate, octyl salicylate, 2 phenylbenzimidazole-5-sulphonic acid, triethanolamine salicylate, 3-(4-methylbenzylidene)-camphor, red petrolatum,3-(4-methylbenzyldine)boran-2-one (methylbenzindinecamphor), benzotriazole, salicylates, phenylbenzimidazole-5-sulfonic acid, methylene bis-benzotriazolyl tetramethylbutyl phenol, avobenzone, 4-isopropyldibenzoylmethane, butylmethoxydibenzoylmethane, octocrylene, octisalate, oxybenzone, bis-ethylhexyloxyphenol methoxy triazine, 4-isopropyl-dibenzoylmethane, metal oxides, octyltriethoxy silanol, alumina, and/or triethoxysilane.

14. The cosmetic composition of claim 1, wherein said composition is a lotion, cream gel, or a spray.

15. The cosmetic composition of claim 1, further including a self-tanner.

16. A sunscreen composition comprising:

one or more photoactives present in an amount of about 0.1 wt. % to about 40.0 wt. % based on a total weight of said composition;

a water dispersible film former comprising an acrylate/$C_{12-22}$ alkylmethacrylate copolymer, polypropylene glycol (PPG)-17/isophorone diisocyanate (IPDI)/dimethylol propionic acid (DMPA) copolymer, and/or VP/polycarbamyl polyglycol ester;

a skin adhesion promoter, present in an amount of about 0.05 wt. % to about 15.0 wt. % based on a total weight of said composition, comprising bis-PPG-15 dimethicone/IPDI copolymer, wherein a weight ratio of said skin adhesion promoter to said photoactives is 1:150 to 1:1;

a color enhancer; and one or more colorants.

17. The sunscreen composition of claim 16, wherein said one or more photoactives is selected from the group consisting of homosalate, octisalate, octocrylene, avobenzone, oxybenzonec, bis-ethylhexyloxyphenol methoxyphenyl triazine, octyltriethoxy silanol, triethoxysilane, titanium dioxide, zinc oxide, and/or alumina.

18. The sunscreen composition of claim 16, wherein said one or more photoactives comprises homosalate, octisalate, octocrylene, and/or avobenzone.

19. The sunscreen composition of claim 16, wherein said water dispersible film former is present in an amount of about 0.5 wt. % to about 3.0 wt. % based on a total weight of said composition.

20. The sunscreen composition of claim 16, wherein said skin adhesion promoter is present in a weight ratio of about 1:150 to about 1:0.1 to the photoactives of said sunscreen composition.

21. The sunscreen composition of claim 16, wherein said skin adhesion promoter is present in a weight ratio of about 1:80 to about 1:1 to the photoactives of said sunscreen composition.

22. The sunscreen composition of claim 16, wherein said color enhancer is present in a weight ratio of about 1:50 to about 1:0.05 to said colorants.

23. The sunscreen composition of claim 16, wherein said color enhancer is present in a weight ratio of about 1:10 to about 1:0.1 to said colorants.

24. The sunscreen composition of claim 16, wherein said color enhancer is present in a weight ratio of about 1:4 to about 1:0.4 to said colorants.

25. The sunscreen composition of claim 16, wherein said one or more colorants comprise hennas, caramels, malva extracts, hibiscus extracts, tyrosines, green teas, glyceraldehydes, ginsengs, erythruloses, ferric compounds, annattos, ultramarine pigments, beta-carotenes, carmines, chrome oxides, titanium oxide, zinc oxide, bismuth compounds, water-soluble dyes, copper powders, guanines, walnut extracts, iron oxides, and/or micas.

26. The sunscreen composition of claim 16, wherein said one or more colorants comprise hennas, caramels, micas, pearl pigments, and/or pearlescent pigments.

27. The sunscreen composition of claim 16, wherein said one or more colorants are present in an amount of about 0.01 wt. % to about 20.0 wt. % based on a total weight of said composition.

28. The sunscreen composition of claim 16, wherein said one or more colorants are present in an amount of about 0.05 wt. % to about 10.0 wt. % based on a total weight of said composition.

29. The sunscreen composition of claim 16, wherein said one or more colorants are present in an amount of about 0.05 wt. % to about 2.5 wt. % based on a total weight of said composition.

30. The sunscreen composition of claim 16, wherein said composition is a lotion, cream gel, or spray.

31. The sunscreen composition of claim 16, further including a self-tanner.

32. A sunscreen composition consisting essentially of:
one or more photoactives present in an amount of about 0.1 wt. % to about 40.0 wt. % based on a total weight of said composition;
a water dispersible film former comprising an acrylate/$C_{12-22}$ alkylmethacrylate copolymer;
a skin adhesion promoter, present in an amount of about 0.05 wt. % to about 15.0 wt. % based on a total weight of said composition, comprising polydiethyleneglycol adipate/isophorone diisocyanate (IPDI) copolymer;
a color enhancer comprising silicone resins, silicone cross-polymers, silicone copolymers, silicone elastomers, silicone resin elastomer gels, silica, fumed silica, amorphous silica, silica dimethyl silylates, hydrophobic modified silica, hydrated silica, and/or silicates; and
one or more colorants.

33. The sunscreen composition of claim 32, wherein said water dispersible film former is present in an amount of about 0.5 wt. % to about 3.0 wt. % based on a total weight of said composition.

34. The sunscreen composition of claim 32, wherein said skin adhesion promoter is present in an amount of about 0.1 wt. % to about 7.0 wt. % based on a total weight of said composition.

35. The sunscreen composition of claim 32, wherein said color enhancer is present in an amount of about 0.2 wt. % to about 2.5 wt. % based on a total weight of said composition.

36. The sunscreen composition of claim 32, wherein said composition has a sun protection factor (SPF) of 4 and said one or more photoactive comprise octisalate, octocrylene and avobenzone present in an amount of about 2.0 wt. %.

37. The sunscreen composition of claim 32, wherein said composition has an SPF of 8 and said one or more photoactive comprise octisalate, octocrylene and avobenzone present in an amount of about 5.0 wt. %.

38. The sunscreen composition of claim 32, wherein said composition has an SPF of 15 and said one or more photoactive comprise octisalate, octocrylene and avobenzone present in an amount of about 8.0 wt. %.

39. The sunscreen composition of claim 32, wherein said composition has an SPF of 30 and said one or more photoactive comprise homosalate, octisalate, octocrylene and avobenzone present in an amount of about 13.0 wt. %.

* * * * *